US007235216B2

(12) United States Patent
Kiselev et al.

(10) Patent No.: US 7,235,216 B2
(45) Date of Patent: Jun. 26, 2007

(54) APPARATUS AND METHOD FOR PRODUCING RADIOPHARMACEUTICALS

(75) Inventors: Maxim Y. Kiselev, Sterling, VA (US); Tomas Vanto, Fairfax, VA (US)

(73) Assignee: IBA Molecular North America, Inc., Sterling, VA (US)

( * ) Notice: Subject to any disclaimer, the term of this patent is extended or adjusted under 35 U.S.C. 154(b) by 0 days.

(21) Appl. No.: 11/380,914

(22) Filed: Apr. 28, 2006

(65) Prior Publication Data

US 2006/0245980 A1    Nov. 2, 2006

Related U.S. Application Data

(60) Provisional application No. 60/676,595, filed on May 1, 2005.

(51) Int. Cl.
*G21C 1/00* (2006.01)

(52) U.S. Cl. .................................. 422/159; 424/1.11

(58) Field of Classification Search ............. 422/159, 422/130; 204/157.2; 376/195, 198; 424/1.11
See application file for complete search history.

(56) References Cited

U.S. PATENT DOCUMENTS

| 3,752,167 A | 8/1973 | Makabe |
| 4,587,989 A | 5/1986 | Mayhew, Jr. |
| 4,614,205 A | 9/1986 | Oroskar |
| 4,700,745 A | 10/1987 | Ellis |
| 5,072,758 A | 12/1991 | Krambrock |
| 5,312,592 A * | 5/1994 | Andersson .................. 422/61 |
| 5,316,042 A | 5/1994 | Lim |
| 5,415,843 A * | 5/1995 | Andersson ................. 422/102 |
| 5,759,513 A | 6/1998 | Nakazawa |
| 5,808,020 A | 9/1998 | Ferrieri |
| 5,932,178 A | 8/1999 | Yamazaki |
| 6,172,207 B1 | 1/2001 | Damhaut |
| 6,375,819 B1 | 4/2002 | Li |
| 6,382,035 B1 | 5/2002 | Nichols |
| 6,390,127 B2 | 5/2002 | Schick |
| 6,453,946 B2 | 9/2002 | Nichols |
| 6,567,492 B2 | 5/2003 | Kiselev |
| 6,599,484 B1 | 7/2003 | Zigler |
| 6,672,336 B2 | 1/2004 | Nichols |

(Continued)

FOREIGN PATENT DOCUMENTS

DE        10320552 A1    11/2004

OTHER PUBLICATIONS

Maeding, DE-10320552 English Abstract from esp@cnet data, Nov. 25, 2004.

(Continued)

*Primary Examiner*—Jill Warden
*Assistant Examiner*—Natalia Levkovich
(74) *Attorney, Agent, or Firm*—Mark Douma (57) ABSTRACT

The invention relates to a system for synthesizing radiopharmaceuticals employing one or more single-use integrated kits of materials, valves and vessels fitted to one or more stationary apparatus in the manner that the kit can be safely ejected and disposed of without manual operations. Fluidic connections on the kits are made with flexible tubing that can be inserted into the various components by hand. This, along with the use of flexible configuration rotary valves, makes it possible to configure them to carry out a variety of processes.

19 Claims, 4 Drawing Sheets

U.S. PATENT DOCUMENTS

| | | |
|---|---|---|
| 6,719,001 B2 | 4/2004 | Ahlgren |
| 6,729,350 B2 | 5/2004 | Schick |
| 2004/0028573 A1 | 2/2004 | Schmitz |
| 2004/0258615 A1 | 12/2004 | Buchanan |
| 2005/0139276 A1 | 6/2005 | Morelle |

OTHER PUBLICATIONS

Fowler et al., "2-Deoxy-2-[18F]Fluoro-D-Glucose for Metabolic Studies: Current Status," Appl. Radiat. Isot., vol. 37, No. 8, pp. 663-668 (1986).

Hamacher et al., "Efficient Stereoscopic Synthesis of NO-Carrier Added [2-18F]Fluoro-2-Deoxy-D-Glucose Using Aminopolyether Supported Nucleophilic Substitution," J. Nucl. Med., vol. 27, No. 2, pp. 235-238 (1986).

Coenen et al., "Recommendation for a Practical Production of 2-[18F]Fluoro-2-Deoxy-D-Glucose," Appl. Radiat. Isot., vol. 38, No. 8, pp. 605-610 (1987).

Knust et al., "Synthesis of 18F-2 Deoxy-2-Fluoro-D-Glucose and 18F-3-Deoxy-3Flouro-D-Glucose with No-Carrier-Added 18F-Fluoride," J. Radioanal. Nucl. Chem., vol. 132, No. 1, pp. 85-91 (1989).

Hamacher et al., "Computer-aided Synthesis (CAD) of No-carrier-added 2-[18F]Fluro-2-Deoxy-D-Glucose: and Efficient Automated System for the Aminopolyether-supported Nucleophilic Fluorination," Appl. Radiat. Isot., vol. 41, No. 1, pp. 49-55 (1'990)

"S9120 PETtrace FDG Microlab," Product Data, Sep. 1996, GE Medical Systems, Milwaukee, Wisconsin.

"PETtrace FDG Microlab Operator Guide," Technical Publications: Direction 2102598 - Revision 1, 1995, pp. T, i-iii, 1-1, 3-1 - 3-10, & 4-1 - 4-18, GE Medical Systems, Milwaukee, Wisconsin.

"S9140 TRACERtab MX(sub)FDG," Product Data, Rev B, Feb.-2003, GE Medical systems, Milwaukee, Wisconsin.

"TRACERlab MX(sub)FDG Operator Manual," Technical Publications: Directions 2335255-100, Version 1, Mar. 2003, pp. T, 5 - 7, 19 - 22, & 34 - 37, GE Medical Systems, Benelux, s.a., Liege Belgium.

"Type 70 Switching Valves," Product Bulletin 114, Jul./1999 Rheodyne LLC, Rohnert Park, California.

"Operating Instructions, Type 70 High Pressure Switching valves, Model 7010 Sample Injector," Jun./2002, Rheodyne LLC, Rohnert Park, California.

"Low Pressure Teflon Rotary Valves," Product Bulletin 104, Aug./1999, Rheodyne LLC, Rohnert Park, California.

"Operating Instructions, Models 5020 . . . Low Pressure Teflon Rotary Valves," Jun./1999, Rheodyne LLC, Rohnert Park, California.

"Rheodyne Low Pressure Switching Valves," Chromatography Source Book C550, 2003/2004, p. 531, Alltech Associates, Inc., Deerfield, Illinois.

\* cited by examiner

APPARATUS AND METHOD FOR PRODUCING RADIOPHARMACEUTICALS

This application claims benefit of application Ser. No. 60/676,595 filed May 1, 2005.

BACKGROUND

1. Technical Field

The invention relates to a system for synthesizing labeled compounds such as [$^{18}$F] 2-fluoro-2-deoxy-D-glucose, and the like, employing various single-use integrated kits of materials, valves and vessels fitted to a fixed stationary apparatus.

2. Background

F-18 compounds, exemplified by [$^{18}$F] 2-Fluoro-2-Deoxy-D-Glucose (hereinafter FDG), have become widely used in nuclear medicine for diagnostic studies using a Positron Emission Tomography (PET) body scanning technique.

Production of $^{18}$F-labeled FDG is, by now, well known. Information can be found in: 1) Fowler et al., "2-Deoxy-2-[18F]Fluoro-D-Glucose for Metabolic Studies: Current Status," Appl. Radiat. Isotopes, vol. 37, no. 8, pp. 663–668 (1986); 2) Hamacher et al., "Efficient Stereospecific Synthesis of No-Carrier-Added 2-[18F]-Fluoro-2-Deoxy-D-Glucose Using Aminopolyether Supported Nucleophilic Substitution," J. Nucl. Med., vol. 27, pp. 235–238 1986; 3) Coenen et al., "Recommendation for Practical Production of [2-18F]Fluoro-2-Deoxy-D-Glucose," Appl. Radiat. Isotopes, vol. 38, no. 8, pp. 605–610 (1987) (a good review); 4) Knust et al., "Synthesis of 18F-2-deoxy-2-fluoro-D-glucose and 18F-3-deoxy-3-fluoro-D-glucose with no-carrier-added 18F-fluoride," J. Radioanal. Nucl. Chem., vol. 132, no. 1, pp. 85–91 (1989); and 5) Hamacher et al., "Computer-aided Synthesis (CAS) of No-carrier-added 2-[18F]Fluoro-2-Deoxy-D-Glucose: An Efficient Automated System for the Aminopolyether-supported Nucleophilic Fluorination," Appl. Radiat. Isotopes, vol. 41, no. 1, pp. 49–55 (1990). See also U.S. Pat. No. 6,567,492 to Kislelev al. (20 May 2003).

Several automatic processing systems capable of production of radiopharmaceuticals, such as $^{18}$F-labeled FDG, have also been described in: 1) U.S. Pat. No. 5,808,020 to Ferrieri et al. (15 Sep. 1998); 2) U.S. Pat. No. 6,599,484 to Zigler et al. (29 Jul. 2003); PCT pub. WO2004093652 by Buchanan et al. (2004-Nov.-04); and 3) German patent DE10320552 to Maeding et al., "Apparatus marking pharmaceutical substances with fluorine isotope, preparatory to positron-emission tomography, locates anion exchanger within measurement chamber" (2004-Nov.-25).

These can be characterized as being stationary systems that do not use any removable components, where all connections of tubes and valves are permanent and do not change in day-to-day operation. Some, such as Zigler et al., describe their systems as multi-batch capable. These have the advantage of being able to save cost by reusing components. That is accomplished by rinsing all vessels and connecting tubing with solvents between production cycles without removing them from the apparatus. It is usually referred to as a Clean-in-Place (CIP) procedure. However, due to the configuration of apparatus, it may be impossible to achieve complete cleaning and sterilization of all components. In addition, the CIP approach requires substantial downtime between processing cycles, which may even exceed the duration of the processing cycle itself. CIP procedures also require extensive validation and may not be acceptable from regulatory standpoint due to the inherent risk of cross-contamination between batches. Finally, such systems cannot be easily adapted for production of multiple different products, because all plumbing components are stationary and cannot be quickly changed in normal operating conditions.

To ameliorate the CIP problems, the following disclose use of removable kits for synthesis of $^{18}$F-labeled compounds, mainly FDG: 1) U.S. Pat. No. 5,312,592 (17 May 1994) and U.S. Pat. No. 5,415,843 (16 May 1995) to Andersson (17 May 1994); 2) U.S. Pat. No. 5,759,513 to Nakazawa et al. (2 Jun. 1998); 3) U.S. Pat. No. 5,932,178 to Yamazaki et al. (3 Aug. 1999); 4) U.S. Pat. No. 6,172,207 to Damhaut et al. (9 Jan. 2001); and 5) U.S. Pub. no. 2004/0028573 A1 by Schmitz et al. (12 Feb. 2004), corresponding to EU patent EP1343533 (2003-Sep.-17). Damhaut et al. disclose a process with a preference for a single-use kit, but the physical aspects of the kit are not well developed. The other four references disclose single-use kit apparatus. The major problem is that they are dedicated to a particular process and are not easily reconfigured. This is an issue because, to save cost, injection molded plastic manufacturing should be used where possible. However, the need for any one radiopharmaceutical may not justify the investment in an injection mold for each one.

In producing FDG and other radiopharmaceuticals, there are a number of difficulties. Radioisotopes produce radiation that can damage some construction materials limiting the selection. Of course, workers must be shielded and cannot be in the presence of the processing apparatus. Such protective shielding used for this purpose must be relatively thick; a minimum 10 cm (4 in.) of lead is typically required to adequately protect personnel. The size of this shielding and its weight depend mainly on the size and dimensions of the processing apparatus. Therefore it is important that such apparatus is made as compact as possible to minimize the cost and weight of shielding. Even after a production run, the apparatus can contain enough residues so that handling the used apparatus is dangerous. A typical decay period of 12–16 hours is needed during which time equipment cannot be accessed by hand. However, to be efficient multiple batches must be processed each day, typically as many as sixteen.

As noted, a disposable kit must not be expensive compared to the value of the final product. This means that it should be made from inexpensive parts and materials and be capable of being reconfigured for different processes. Because of the short half-life of some radioisotopes (109 min. for the $^{18}$F), these products must be produced in relatively large quantities to allow for decay during delivery to the patient from a manufacturing facility. Therefore, it is necessary to perform this process automatically using systems placed within the protective shielding without manual intervention. To increase production, it is useful if the automated systems can be quickly and safely re-loaded with materials needed for the next production run.

Because of the short radioisotope half-life, production facilities are distributed in many geographical locations. Since different skill sets are required to run a radioisotope generator and a chemical process, preparation of kits on-site requires more personnel than if kits were prepared in advance at a central location. (Central preparation should also improve quality control.) However, some chemicals have a short shelf life unless kept sealed.

Another difficulty is that the cost and weight of lead shielding makes it desirable to limit the volume taken up by processing apparatus as much as possible. Typically, sizes less than 40 cm (16 in.) deep by 40 cm (16 in.) high by 20 cm (8 in.) wide would be desirable.

SUMMARY

In a system for the preparation of radiopharmaceuticals that includes a fixed processor, production can be improved by using disposable kits, in particular, kits having a vertical plate parallel to the processor front face and a sensibly horizontal plate mounted to the vertical plate. The vertical plate mounts a plurality of fluidic interconnections having mating connections mounted on the processor front face as well as rotary slide valves that interface with rotary actuators protruding from the processor front face. Mating and interfacing is accomplished by translating the vertical plate horizontally with respect to the processor. The horizontal plate mounts one or more reservoirs or vials providing reagents on the top with reactor and collection vials on the bottom. It also can mount one or more filter cartridges. Connections between components on both plates are made with flexible plastic tubing.

The rotor and stator of the rotary slide valves are contained within circular cavities in the vertical plate that become the valve housings with fluid input and output through holes in the plate at the end of the cavity. The stator is at the end of the cavity and has corresponding holes that are appreciably smaller than the tubing used. Although tubing can be inserted by hand, the stator is an elastomeric material having sufficient friction to hold and seal the tubing once inserted without further fixturing.

The rotor is a hard plastic having one or more channels or slots on a side facing the stator. Rotating the rotor makes and breaks fluid connections between holes in the stator. The side facing away from the stator has a slot for engaging a blade end of a spring-loaded rod that is driven by a rotary actuator in the processor.

The processor has a reactor vessel heater that can be moved up to surround a reactor on the bottom of the horizontal plate.

To reduce cost and assembly time and provide increased rigidity to the vertical plate as it is pushed against the spring loaded actuators and fluid connections, the horizontal plate is mounted with integral fingers that snap fit into corresponding holes in the vertical plate.

Both plates, rotors, stators and connecting tubes are manufactured from radiation resistant injection-molded or extruded plastic. However, the arrangement of vials and valves means that the fluid circuits can be easily re-configured for different processes by using various combinations of different rotors and stators and repositioning interconnecting tubes.

Linear translation of the kit is accomplished with a linear actuator mounted on the processor and connected to a kit mounting structure having vertical guides that, during processing operations, surround slides that are part of the kit vertical plate. The kit is supported from underneath by rods or similar that extend out from the processor. At the end of a run, the linear actuators disengage the kit from the processor interface and push the kit off the end of the rods so that the kit slides down out of the guides into a shielded collection bin below.

The collection bin is arranged so that kits slide into a chamber out of a line of sight from the processor allowing an operator to insert a new kit by hand without being irradiated. Optionally, a cassette feeder that drops new kits from a magazine into the kit vertical guides could be used.

Due to the short half-life, radiopharmaceuticals are produced at dispersed geographic locations near the site of isotope production. Preferably, kits are configured at a central location off-site. During this configuration process, septum-sealed vials are filled with reagents. These vials are put in place on the horizontal plate, but left sealed. After installing the kit, hypodermic needles attached to flexible tubing are pushed through the septa.

Radiopharmaceuticals that require more than one heated reactor may be made using two or more processor/kit modules in sequence. The modules are designed to be less than 16 cm (6 in.) wide so that a typical radiation enclosure can accommodate up to four modules.

DETAILED DESCRIPTION

The following describes the best way of carrying out the invention. All specific materials, sizes, dimensions, suppliers and parts mentioned are provided as an example only to enable easy reproduction of the invention and are not limiting. Other materials, dimensions and parts from different suppliers can be used to achieve the same effect.

Figure 1A:
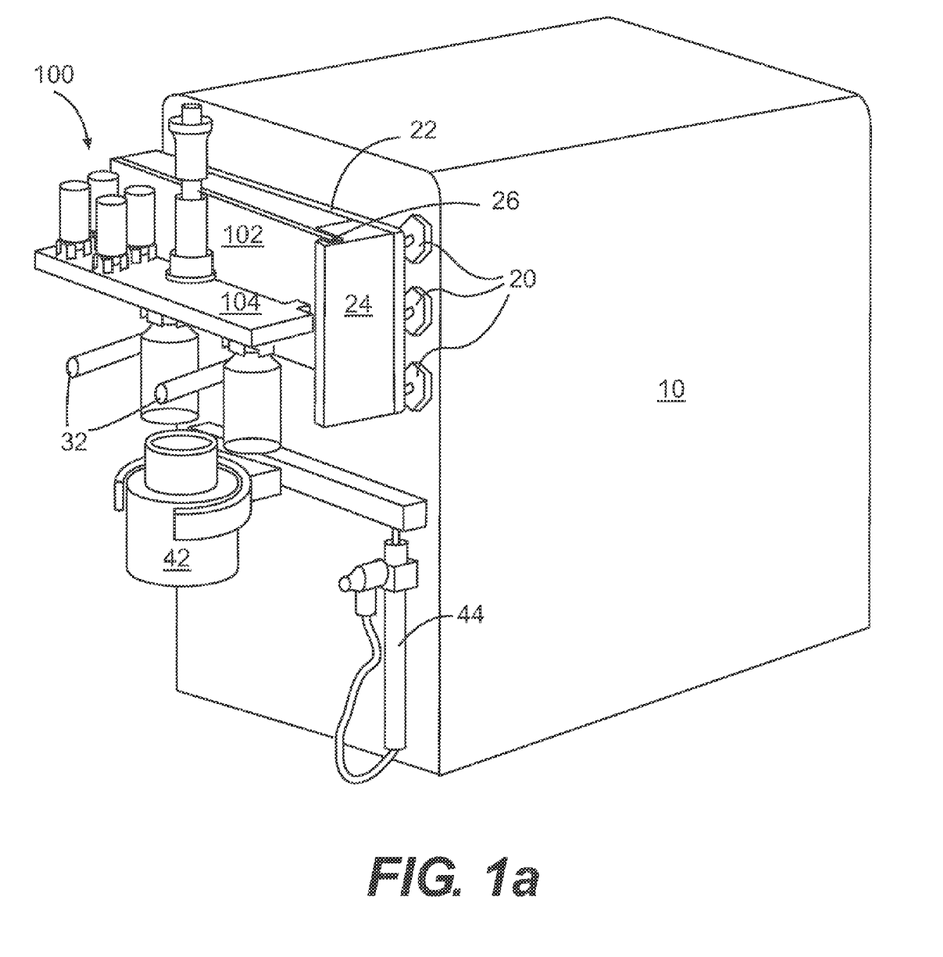
FIG. 1a illustrates a general view of the invention showing a processor and a demountable kit.

FIG. 1a illustrates, generally, a processing system utilizing the invention shown from the top, front, and one side. There are two main sections, a stationary synthesizer section 10 and a removable kit 100. Depending on the process, the synthesizer section may have various inputs and outputs, namely: fluid or gas input/output lines; compressed air, nitrogen, or vacuum lines; an electric power input; and electronic control cables. The stationary synthesizer 10 may also contain, as needed: various sensors used for feedback control such as pressure or radioactivity sensors; electric relay controlled solenoid valves used to control pneumatic devices with magnetic position sensor feedback; manually adjustable needle valves for gas flow control; a local vacuum pump; and a microprocessor-based control module. The above devices are employed in the manner commonly used in similar systems and well known to any person skilled in the art.

The stationary synthesizer 10 also has, mounted on a side, linear pneumatic actuator kit positioners 20 (three are shown on one side) connected to a kit mounting plate 22 having two side supports 24 with slots 26 aligned with a sensibly vertical plate 102 of the kit 100. The slots 26 (not shown to scale) are wide enough to permit the kit 100 to slide up and down. Two kit support rods 32 protrude from the synthesizer underneath the kit support the bottom of the vertical plate 102. This version also contains a reagent heater 42 that is raised up and down by two linear pneumatic actuator heater positioners 44 (one is shown). When the kit has finished processing a batch, the reagent heater (if used) is lowered and the kit positioners 20 (located behind the hex mounting nuts with protruding pistons shown) can push the kit away from the synthesizer off the end of the support rods 32 into a shielded bin below (not shown).

Figure 2:
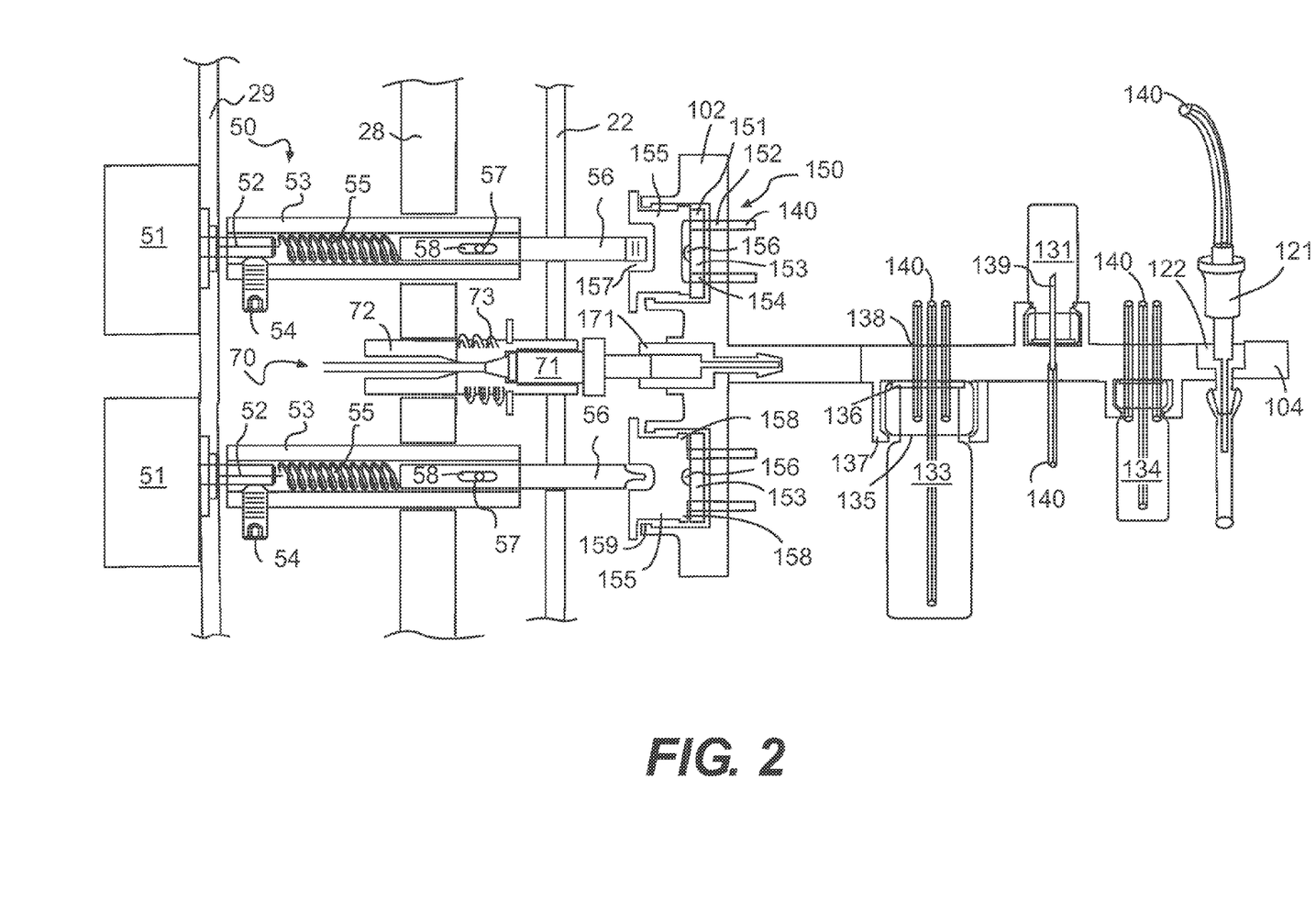
FIG. 2 shows a detailed cross-section of the invention illustrated in FIG. 1.

As generally illustrated in FIG. 1*a* and shown in detail in FIG. 2, there can be a variety of reagent bottles, cartridge filters, reaction vessels and collection bottles.

Figure 1B:
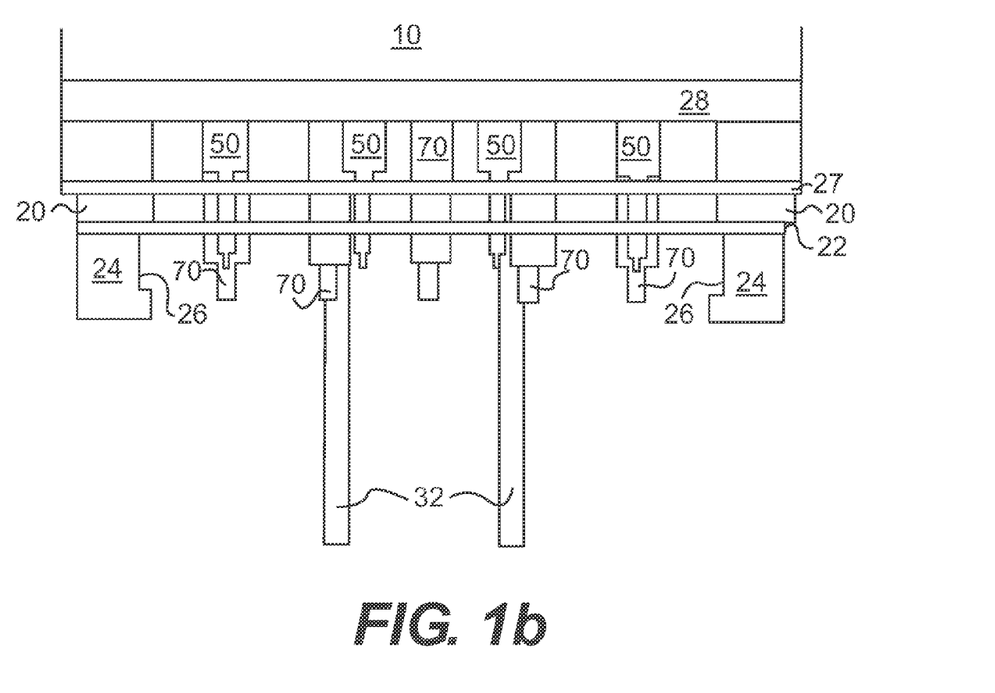
FIG. 1b is a top view of a portion OF he detail of the interface between the kit and the processor.

FIG. 1*b* is a top view of the kit mounting apparatus and interfaces to the processor 10. The front of the processor box is plate 27. An intermediate actuator guiding plate 28 has clearance holes for the linear actuators 20, a plurality of rotary actuators 50 and fluidic connections 70 (discussed below). In operation, the kit 100 would be contained within slots 26 in side supports 24 that are attached to kit mounting plate 22. Support rods 32 for the kit 100 extend out from the front plate 27. Heater 42 is not shown in this view.

Figure 1C:
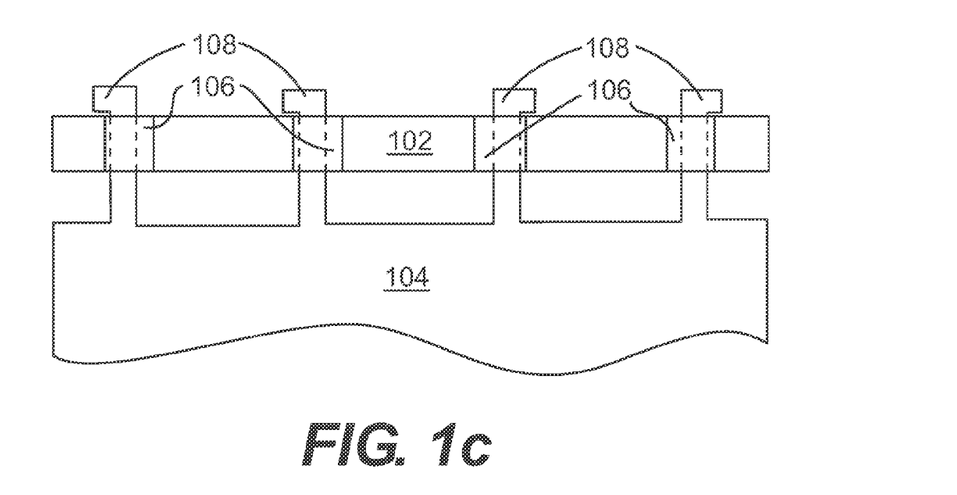
FIG. 1c illustrates how two plates making up the kit snap together.

FIG. 1*c* illustrates how horizontal kit plate 104 is connected to sensibly vertical kit plate 102 with a plurality of rectangular cross-section snap fingers 106. These are formed integrally with plate 104 and protrude from it into rectangular holes 108 in plate 102. The fingers 106 have catches mounted on the end and the location of fittings and holes on the plates is such that when the plates are forced together, the fittings lock around the far side of plate 102.

FIG. 2 illustrates a vertical cross section of the kit 100 and both a plurality of mechanical interfaces 50 and fluidic ones 70 to the processor 10. Details of these interfaces will be given below. Three fixed plates are shown: the front of the processor 27, actuator guiding plate 28 and an internal pneumatic actuator 51 mounting plate 29. (The kit mounting plate 22 and kit mounts 24 are omitted for clarity.)

Plate 104 has mounted thereon a plurality of filtration cartridges 121. These are mounted on the plate 104 with Luer-type receptacles 122. Also mounted on plate 104 are a variety of reagent vials 131, a reactor vessel 133, and a collection vial 134. The number, size and type will depend on the process.

The vials (generally referred to as "serum vials") are commercial glass bottles with aluminum crimp seals 135 that hold elastomer seals 136 to the mouth of the vial. The aluminum crimp seals 135 are held to the plate by protruding snap fingers 137. When vials are filled with reagents, stainless steel needles 139 connected to tubing 140 can be inserted through the elastomer seals 136 into the vials just prior to use of the kit. In other cases, the tubing is inserted through undersized holes in the seals 136. The Luer-type connectors for the fluidic interface to the processor and cartridges have barb-type tube fittings. Various lengths of the flexible polymer tubing 140 can be used to make all necessary connections.

In some cases, gravity is used to control liquid position inside the vials, dictating the convenience of a using a horizontal plate, but that is not always essential. On the other extreme, a single horizontal plate could be used with a processor interface in a horizontal plane, but this would require kit release actuators on the side supports 24 or a combination of vertical and horizontal linear actuators. The combination of a vertical processor interface plate with a horizontal vial mounting plate connected at the center of the vertical plate does reduce overall dimensions of the kit.

A major advance of this invention over the prior art is represented by the rotary slide valves 150 located in the vertical plate 102. Two are illustrated in the cross-section, but eight are contemplated for a typical kit. These are constructed inside a round cavity 151 in the plate having tubing pass through holes 152. The stator 153 is comprised of an elastomer (e.g., VITON® or Buna N) having enough friction and having under-sized holes 154 so that tubing 140 can be directly inserted into them and will remain in place even under hydrostatic pressure. This avoids the use of fittings and their cost. The rotor 155 is preferably comprised of plastic and has a channel 156 cut into the side facing the rotor and a slot 157 to allow it to be turned by a mechanical actuator. A circular rim 158 allows the rotor to be snap fit into the plate 102 past its rim 159 so that the stator is retained during shipment.

The rotary valve mechanical actuator 50 is driven by a pneumatic rotary actuator 51 with an output shaft 52 that is held in a rotating coupling 53 by a setscrew 54. The transfer tube contains a spring 55 that pushes a screwdriver type valve engagement 56 having a pin 57 that slides in a slot 58 in the tube. The pin 57 insures that screwdriver type actuator 56 turns together with shaft 52 while being free to move back and forth and transfer the force of spring 55 to the rotor 155 which achieves a leak tight interface with stator 153. In one version, the actuators 50 rotate through 90° steps. This is shown by the two positions of the rotors 156.

Fluidic connection to the kit is made via commercial Luer-type female receptacles 171. The connection to the processor 10 is completed with spring-loaded couplings 70. Commercial Luer type male fittings 71 are screwed into tube 72 (threads not shown) that is positioned by plate 28 and urged forward by spring 73. Both fittings are barb-type and connections to tubing 140 are made in a conventional manner.

Prototype Example:

A laboratory prototype of both a synthesizer 10 and kits 100 were constructed. On the synthesizer 10, six parallel pneumatic linear actuators 20, three on each side, with a bore of 15 mm and a stroke of 75 mm were mounted on the front panel. The support rods 32 were 5 mm dia. and extended 70 mm in front of the synthesizer to prevent the kit from falling down unless the kit holder is in a fully extended position. In a retracted position, the back of the kit 100 is pulled into valve actuators 50 and Luer fittings 70 with a force of over 1000 N. In extended position, the kit is allowed to drop freely into a prepared shielded receptacle placed under the synthesizer. To install the kit, an operator shifts the kit mounting plate 22 to a middle position, and slides the kit into the slots 26 from the top. After that, the shielding door is closed and pneumatic cylinders are remotely engaged to pull the kit mounting plate 22 with the kit 100 back and attach it to the synthesizer 10 so that the processing can be carried out. Finally, upon completion of the processing, extending the kit mounting plate 22 forward, beyond the guiding rods 32 and allowing the kit 100 to drop into a prepared receptacle removes the kit. This last step is accomplished automatically, without operator intervention or opening the shielding door.

To achieve the heating and evaporation processes necessary for radiotracer production, the synthesizer was equipped with a cylindrical aluminum block reagent heater 42. This is heated with compact cylindrical cartridge, Omega Engineering Co. (Hartford, Conn.) model CSS-10150/120 and PT100-type temperature probe model PX177-050AI. The heating block can be heated to 200° C. The heater positioner 44 was driven with two 6 mm bore pneumatic cylinders having an up and down travel of 50 mm. When in the upper position, the heating block is in contact with the reactor vessel 133 mounted on the kit 100. When in the lower position, the heating block is clear of the reactor and other parts of the kit allowing automatic kit ejection.

The synthesizer 10 was equipped with eight spring-loaded rotary valve actuators 50, arranged in two rows of four, spaced 30 mm between centers vertically and horizontally.

Festo AG & Co. (Esslingen, Germany) Swivel Module DSM-6-90-P rotary actuators, equipped with model SME-10-KL position sensors and model CPA-SC solenoid valves, were used for the rotary pneumatic actuator motor 51. These can operate over a pressure of 3.5–8 bar and produce 0.15 Nm torque at 6 bar. However, many laboratory compressors do not operate comfortably above 5 bar (75 psi) so the limit was 0.13 Nm The rotation coupling 53 was stainless, 51 mm long having an ID of 5 mm and a slot 1.6 mm×7 mm. The valve engagement rod 56 was stainless 43 mm long with an OD of 4 mm. This material and dimensions are not critical. The spring 55 was about 25 mm long x 4 mm OD. The dimensions and spacings were designed, so that the springs were compressed approximately 5 mm, to 20 mm, in length to provide a force of 30 N There is a tradeoff for the force on the rotor. A greater force on the rotor 155 provides a tighter seal against the stator 153 and better leak resistance. However, this also requires a larger torque to turn the rotor. The 30 N force was enough to prevent leaks up to 100 kPa (14.5 psi) which is adequate for processing in the kit 100. However, it was found that when a force of more than 45 N was used, the rotary actuators could not easily turn the stator; they were sticky. (Actuators with more torque are available, but they could take up too much space.) Commercial standalone rotary slide valves do not have this problem. The rotor and stator are generally made from hard materials, e.g., ceramics that can be highly polished, or from low coefficient-of-friction materials such as TEFLON®. However, these commercial rotary valves are expensive, not disposable, and require fittings to hold connecting tubing.

The spring loaded coupling adapter housing 72 was made of brass and equipped with a standard Luer fitting, Upchurch Scientific p/n P-619, made from polypropylene. The spring 73 was selected to provide about 34 N when compressed 6.6 mm or about 13 N when compressed the same 2.5 mm as the valve springs 55. This provided an adequate seal for the Luer-type fittings.

A number of conventional components, not illustrated in drawings, were also included in the synthesizer 10. To transfer liquids between reagent tubes and reactor and to achieve evaporation, it is necessary to apply vacuum to various parts of the kit. The synthesizer 10 was equipped with a compact two-head diaphragm type vacuum pump, model 85.3KTI supplied by KNF Neuberger (Freiburg, Germany). This vacuum pump can supply vacuum down to 2 mbar and was connected with other system components by means of 3 mm OD polypropylene tubing.

The synthesizer 10 has minimal pathways and elements that come in contact with radioactive material, so that residual radiation inside the shielding after removal of the kit 100 is minimized to safe levels, allowing servicing and reloading the synthesizer for the next processing cycle. All plumbing connections within the synthesizer were made with 1.59 mm OD and 3 mm OD tubes made of PEEK (an acronym for polyetheretherketone) or polypropylene. Fittings employed to connect tubes to valves inside the synthesizer and to the kit are flangeless ¼ in. dia.-28 threads/in. flat bottom threaded fittings made of PEEK or polypropylene and equipped with TEFZELL® ferrules. All tubes, fittings and ferrules can be obtained from Upchurch Scientific (Oak Harbor, Wash.).

The synthesizer was also equipped with an array of sensors and actuators including temperature probe type RTD PT100 and pressure sensor type PX177-050AI, supplied by Omega Engineering Co. (Hartford, Conn.), at least one radioactivity sensor based on silicone diode backed scintillator, and other routine sensors and actuators necessary to monitor important process parameters and allow for operator control of the synthesis process.

To control the flow of inert gases and vacuum as well as to provide an external waste collection container, a number of solenoid valves and a needle valve were installed inside the synthesizer 10. These components do not come in contact with radioactive material and therefore do not require frequent replacement.

The removable kit 100 was made from machined acetal plastic. (Commercial quantities would use an injection-molding process.) The vertical plate 102 was about 130 mm wide and 50 mm high.

To make the rotary valves 150, eight round cavities 151 were machined with an internal diameter of 10 mm spaced to interface with the rotary valve actuators 50 on the processor 10. Each valve 150 was comprised of a stationary stator 153 made of VITON® rubber having a Shore A hardness of 65–75. Buna N or a silicone rubber can also be used, also preferably having a Shore A hardness of 65–75. The rotor 155 was made from polypropylene. Each stator 153 is 3.2 mm (0.125 in.) thick and 10 mm dia. and fits tightly into a cavity 151 in the vertical plate 102. Each stator can be molded with two, three or four holes 154 to accommodate the desired number of connecting tubes. Holes 154 are 1 mm diameter to provide a leak tight fit for 1.59 mm OD tubes without use of any fittings. The pattern of the holes in stators 153 corresponds to slightly larger 1.6 mm dia. holes in the vertical plate 102 through which tubes are connected. Each rotor 155 fits loosely into the cavity and is interfaced on the backside with a rotating actuator engagement 56, which can rotate it back and forth 90° driven by the pneumatic swivel module type 51. As noted above, the rotor is pressed into the stator by the force of spring 55. The face of each rotor has one or more depressions (groves) 1 mm wide and 1 mm deep that can connect holes in the stator. When a rotor is turned, a different pair of holes will be connected thus changing the fluid flow path. By using different orientations or depressions in the rotor and different placements and numbers of holes in the stator, several different flow patterns can be achieved without the need to replace the main vertical plate 102. Using interchangeable rotor and stator combinations, one can achieve flexible plumbing patterns without the additional cost of modifying large components.

The horizontal plates (several were made) 104 were about 130 mm wide and 75 mm long. Horizontal plates 104 also had at least two female Luer receptacles 122 to mount filtration cartridges and contained receptacles to hold at least four crimp top vials 131 in inverted position on the top side of the plate and at least two larger crimp top vials 131 and 134 on the bottom side. The horizontal plate is attached to the vertical plate 102 by means of at least four pins 106 equipped with locking teeth to allow snap-in assembly without the use of glue or fasteners. The horizontal plate, when attached to a vertical plate, provides structural strength and prevents the vertical plate from deforming under stress when attached to the synthesizer.

Six or more crimp-sealed vials, pre-filled with pre-measured amounts of reagents as necessary or empty, are attached to the top and bottom sides of the horizontal plate 104. The entire kit can be assembled and preloaded with reagents prior to use so that automated processes can be accomplished without extensive preparation. Empty vials, such as a reactor and a product collection container placed on the bottom side of the horizontal plate, are equipped with septa with 1 mm diameter holes through which the 1.59 mm OD tubes are pre-inserted when the kit is assembled. The vials attached to the top side of the plate are pre-loaded with reagents and equipped with sealed septa so that reagents remain intact during storage and shipping. During processing, reagents are withdrawn from these vials by means of 22 gauge (0.9 mm OD) needles, which are connected to 1.59 mm tubes. The needles are pre-inserted into the guiding holes in the plate, but they do not penetrate the septa of the vial until the kit is ready to use. These needles are inserted immediately before automated processing begins. This allows use of highly sensitive reagents and greatly reduces the chances of operator error during preparation.

The size and shape of reagent vials and reactors can be easily changed without modifying the carrying plate. The vial holders are designed to interface with standard crimp-top necks of vials. Reagent vial receptacles are fitted to hold 11 mm and 15 mm crimp-top vials, while reactor and collection vial receptacles are equipped for 20 mm crimp top serum vials. A wide variety of vials, ranging in volume from 0.1 to 25 ml, can be used with the kit providing the flexibility needed to accommodate a multitude of different chemical processes.

The entire kit, including all necessary reagents, filters, tubes and fittings, can be pre-assembled and pre-loaded with chemicals before it is delivered to an end user. This allows for much better quality control, reproducibility and reliability of synthesis by eliminating operator errors. This arrangement also allows for sterilization of the kit using gamma sterilization or an ethylene oxide method before use. Removing and re-furbishing of the kit is also possible if needed.

All plumbing within the kit is made by 1.59 mm OD polypropylene tubing; except for an evacuation tube for connecting vacuum to the reactor which can be made with 3 mm OD, 1.59 ID tubing. The tubes are connected to vials and valves by inserting them into pre-formed holes in rubber septa of the vials and stators of the valves. Thus, use of threaded fittings is eliminated. Barbed fittings are used where necessary to connect tubes to Luer adapters needed to connect filters and cartridges. It is important to note that all tubes are free hanging, and may be re-routed in any direction to connect any port of any valve to any other valve or vial with no restrictions, unlike what is frequently the case with existing similar kits.

All materials used in kit construction, polypropylene, VITON®, Buna N and PEEK are carefully selected to provide the best chemical and radiation resistance. VITON® and Buna N are, generically, cross-linked thermoplastic polyolefin elastomers. Materials with low radiation resistance such as TEFLON®, silicon rubber, polyurethane etc. should be carefully avoided. Silicone rubber can be used, however, when it is essential to avoid possible contamination with fluorides which are contained in the other preferred elastomers.

Multi-stage Synthesis:

It is frequently necessary to conduct multi-stage synthesis. Although each kit contains a sufficient number of reagent vials, reactors, and filter holding positions to conduct a typical one-stage process, such as FDG production, it will be necessary to use multiple modules for more complex processes, such as F-DOPA production. As discussed, the kits 100 can be easily reconfigured for a many different processes. Although limited to one reactor, a module of processor 10 with kit 100 is only 16 cm (6 in.) wide so that three or more modules can be placed in a typical shielded enclosure. Each module can be equipped with a different kit especially designed for one stage of the multistage process.

In this case, all reagents needed in the first stage to produce intermediate product #1 are placed in kit #1 and attached to synthesizer #1. After processing the first stage, the intermediate product is passed to kit #2 via tubing connecting the two processors (or directly between kits if more convenient) where reagents needed for the second stage are installed. In this way, four and, possibly, five stage processes can be carried out in one enclosure using the same basic processors and, especially, single-use kits.

EXAMPLE

The following example is provided for illustration only and is not limiting in the sense that many other radiotracers can be produced using the system.

Figure 3:
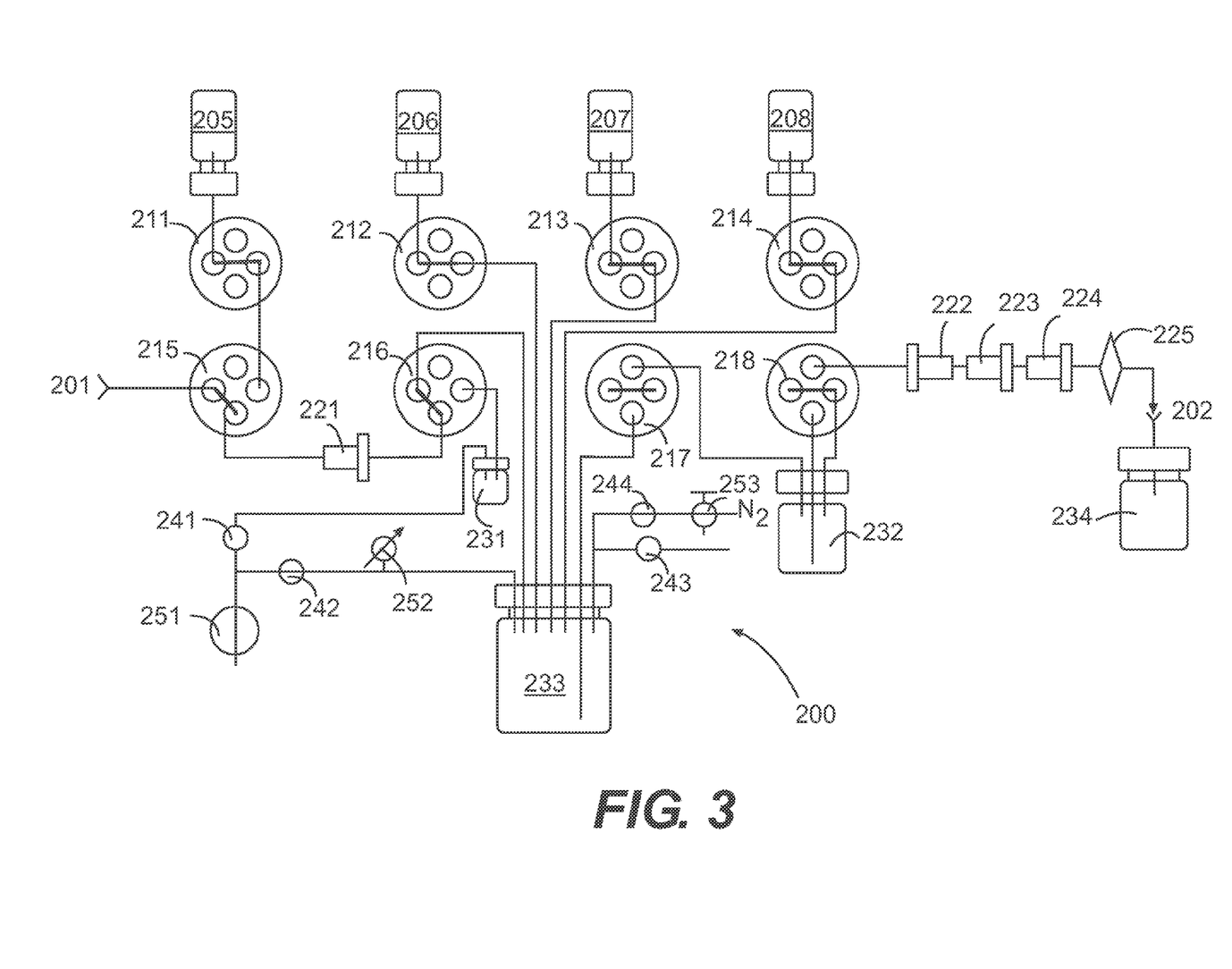
FIG. 3 shows a process flow diagram taken from a process controller for an example radiopharmaceutical, FDG.

FIG. 3 shows a schematic process 200 for FDG synthesis that can be obtained by configuring the kit 100. Input from a cyclotron is represented by 201 Reagent vials 205–208 are represented on the top of the diagram and contain all reagents and solutions necessary for the synthesis. The top row of four rotating valves 211–214 are configured as two port valves, with top and bottom port unused and not connected. They are shown in open position in the diagram, however they will be normally closed at the beginning of the process and only open to add reagent when necessary. Reactor vessel 233 is schematically represented in the center of the illustration. The smaller vessel 232 to the right is used to collect and homogenize the reaction mixture before filtration through the sterile filter 225. QMA cartridge 221 is connected between valves 215 and 216, which are configured as three port switching valves, and purification cartridges 222, 223, and 224 are connected to valve 218, which is configured as a four-port valve. Stationary solenoid valves 243 and 244 mounted inside the synthesizer control nitrogen flow into the reactor. Solenoid valve 242, when opened, connects vacuum pump 251 to the reactor. Pressure is monitored by the pressure sensor 252.

The synthesis of FDG is carried out according to method described by Hammacher et al. Synthesis of the FDG itself is not considered to be part of this invention and only a basic description of a process is included here.

The usual synthesis of FDG is a two-step process consisting of two chemical reactions: a nucleophilic F-18 fluorination followed by a hydrolysis step. The fluorination step incorporates an F-18 label into an organic precursor, 1,3,4, 6-tetra-O-acetyl-2-O-trifluoro-methanesulfonyl-βD-mannopyranose (mannose triflate).

The substitution reaction is accomplished by combining a phase transfer catalyst, with 18F fluoride extracted from an irradiated target material. To extract 18F fluoride, the irradiated water enriched with an O-18 isotope and containing F-18 fluoride is directed through QMA cartridge 221 and into O-18 collection vessel 231 by way of valves 215 and 216. F-18 fluoride remains trapped in QMA cartridge 221 and is eluted by passing a mixture of KRYPTOFIX® 222 with potassium carbonate through the cartridge and into reaction vessel 233 by way of valves 211, 215 and 216.

The mixture is evaporated for 8–10 min. in a stream of inert gas ($N_2$ or He) via flow regulating needle valve 253 by opening valves 242, 243 and 244 and heating the reactor 233 to 80–100° C. and then dried in vacuum by closing valve 243 for 1–2 min. After cooling the reactor by lowering block 42 (see FIG. 1a), a solution of the mannose triflate in acetonitrile is added to this dried mixture by way of valve 212 and incubated at 85° C. for 3 min. The resulting solution is heated and dried in a stream of inert gas ($N_2$ or He).

The hydrolysis step, as exemplified by a base-catalyzed hydrolysis of the acetyl protecting groups, generates the free hydroxyl groups of the final drug product. A predetermined amount of solution of NaOH in water is added by way of valve 214 as a hydrolyzing reagent to the dry fluorinated mannose triflate and the resulting solution is heated at 75–90° C. for 3–5 min. in a stream of inert gas by opening valves 243 and 242 to achieve complete removal of acetyl groups.

To purify the resulting mixture and leave a solution of FDG in water, it is diluted in 5 ml of water added through valve 213 and filtered through purification cartridges 222, 223, and 224 and particle filter 225 by way of valve 217, homogenization vessel 232, and valve 218 ultimately sent through output 202 to external collection vessel 234.

TEFLON® and TEFZEL® are registered trademarks of E. I. Du Pont de Nemours & Co. for synthetic resinous fluorine-containing polymers. TEFLON® is also known as polytetraflourethelne. VITON® is a registered trademark of Dupont Dow Elastomers L.L.C. for synthetic rubber and rubber compositions, more specifically, it is a cross-linked thermoplastic polyolefin elastomer, as is Buna N, whereas silicone rubber is high temperature vulcanizing polyorganosiloxane elastomer. KRYPTOFIX® is a registered trademark of MERCK KGAA Limited Partnership for a phase transfer catalyst, namely, a polycyclic crown ether that forms a stable cryptate with potassium cations. KRYPTOFIX® 222 is also known as cryptand 222. All of these trademarks have designated the same goods for several decades and are readily available under the trademarks from many suppliers. Irrespective of the survival of the marks, those skilled in the relevant arts will be able to obtain the material used in carrying out this invention for the indefinite future.

While the best modes have been described with particular examples, the invention is only limited by the appended claims. In particular, it was convenient to construct prototypes from metal and plastic plates. However, the structures are not so limited as long as the defined functions can be carried out. For example, planar structures could be made from a lattice-work. Many other equivalent structures will occur to those with ordinary skill in this art. The terms vertical, horizontal, up, and down are defined in the usual manner with respect to gravity.

Note that all documents referenced herein are hereby incorporated by reference in their entirety.

What is claimed is:

1. A synthesizer for producing radiopharmaceuticals comprising:
   a) a stationary processor having a disposable kit interface planar structure disposed substantially vertically and at least:
      i) a plurality of rotary actuators protruding horizontally from said interface surface,
      ii) a plurality of push-on fluidic connectors protruding horizontally from said interface surface, and
      iii) structure for releasably interfacing a disposable kit to said rotary actuators and push-on connectors by means of linear actuators that provide translation in a horizontal direction; and
   b) at least one disposable kit having:
      i) a processor interface planar structure disposed substantially vertically containing at least:
         1) a plurality of rotary slide valves having rotors adapted to interface with said rotary actuators and apertures for making fluidic connections to flexible tubing, and
         2) a plurality of push-on fluidic connectors adapted to interface with said processor push-on fluidic connectors and having fittings for making fluidic connections to flexible tubing, and
      ii) a reagent and reactor vessel mounting structure affixed to said processor interface planar structure and disposed generally horizontally opposite said processor containing at least:
         1) a plurality of vessel mounting structures, said mounting structures having fittings for making fluidic connections to flexible tubing, and
         2) a plurality of flexible tubes for connecting said fittings of one vessel mounting structure to another and to said rotary slide valve apertures and push-on connectors.

2. The synthesizer of claim 1 wherein said processor structure for releasably interfacing a disposable kit further comprises a pair of side supports with slots disposed to allow said kit processor interface planar structure to slide vertically and at least one support rod protruding horizontally form said processor and having a shorter length than the maximum extension of said linear actuators.

3. The synthesizer of claim 1 wherein said processor further comprises a vessel heater affixed to actuators that move in a vertical direction with sufficient upward extent to heat a reactor vessel attached to said kit and sufficient downward extent to clear said reactor vessel during horizontal kit translation.

4. The synthesizer of claim 1 wherein said kit processor interface planar structure has a plurality of holes and said kit reagent and reactor vessel mounting structure has a plurality of corresponding fingers having a curved ends, said holes and fingers disposed so that insertion of said fingers in said holes locks said reagent and reactor vessel mounting structure to said processor interface planar structure.

5. The synthesizer of claim 1 wherein said kit rotary slide valves each comprise a circular cavity in said processor interface planar structure having a base with at least one tubing pass through hole, an elastomer planar stator disposed in said cavity having corresponding holes sufficiently undersized to secure tubing inserted therein, and a two-sided planar rotor disposed adjacent said stator having at least one fluidic channel on the side adjacent said stator and a rotary actuator engagement feature on the opposite side.

6. The synthesizer of claim 5 wherein said kit rotary slide valve rotor is comprised of a radiation resistant polymer selected from the group consisting of VITON and Buna N rubbers and having a Shore A hardness of about 65–75.

7. The synthesizer of claim 6 wherein said rotary valves are about 10 mm in diameter and said rotary actuators have spring loaded rotary valve engagements providing a force against said rotor in the range of about 30–45 N.

8. The synthesizer of claim 1 wherein the maximum horizontal width of said processor and said kit in a direction parallel to said interface structures is less than about 16 cm.

9. The synthesizer of claim 1 further comprising a radiation shielded container disposed below said structure for releasably interfacing a disposable kit so that after release said kit falls into said container.

10. A disposable kit for producing radiopharmaceuticals in conjunction with a stationary processor comprising:
   a) a plurality of rotary slide valves having rotors with engagement features adapted to interface with rotary actuators and apertures for making fluidic connections to flexible tubing;
   b) a plurality of push-on fluidic connectors with openings adapted to interface with mating push-on fluidic connectors and having fittings for making fluidic connections to flexible tubing, wherein said plurality of rotary slide valves and said plurality of push-on fluidic connectors are arrayed on a processor interface planar structure and oriented to interface in a single processor direction; and c) a reagent and reactor vessel mounting structure affixed to said processor interface planar structure and disposed generally horizontally opposite said processor direction and containing at least:
1) a plurality of vessel mounting structures, said mounting structures having fittings for making fluidic connections to flexible tubing, and
2) a plurality of flexible tubes for connecting said fittings of one vessel mounting structure to another and to said rotary slide valve apertures and push-on connectors.

11. The disposable kit of claim 10 wherein said kit processor interface planar structure has a plurality of receptacles and said kit reagent and reactor vessel mounting structure has a plurality of corresponding fingers having a curved ends, said receptacles and fingers disposed so that insertion of said fingers into said receptacloes locks said reagent and reactor vessel mounting structure to said processor interface planar structure.

12. The disposable kit of claim 10 wherein said kit rotary slide valves each comprise a circular cavity in said processor interface planar structure having a base with at least one tubing pass through hole, an elastomer planar stator disposed in said cavity having corresponding holes sufficiently undersized to secure tubing inserted therein, and a two-sided planar rotor disposed adjacent said stator having at least one fluidic channel on the side adjacent said stator and a rotary actuator engagement feature on the opposite side.

13. The disposable kit of claim 12 wherein said kit rotary slide valve rotor is comprised of a radiation resistant polymer selected from the group consisting of VITON and Buna N rubbers and having a Shore A hardness of about 65–75 and a diameter of about 10 mm so that a force against said rotor in the range of about 30–45 N is sufficient to provide a leak tight seal against a hydrostatic pressure of 100 kPa (14.5 psi).

14. A method of producing radiopharmaceuticals comprising the steps of:
1) providing a stationary processor having a disposable kit interface planar structure disposed substantially vertically and at least a plurality of rotary actuators protruding horizontally from said interface structure, a plurality of push-on fluidic connectors protruding horizontally from said interface structure, and structure for releasably interfacing a disposable kit to said rotary actuators and push-on connectors by means of linear actuators that provide translation in a horizontal direction; and 2) providing at least one disposable kit having:
a) a processor interface planar structure containing at least a plurality of rotary slide valves, having rotors adapted to interface with said rotary actuators and apertures for making fluidic connections to flexible tubing, and a plurality of push-on fluidic connectors adapted to interface with said processor push-on fluidic connectors and having fittings for making fluidic connections to flexible tubing, and
b) a reagent and reactor vessel mounting structure affixed to said processor interface planar structure and disposed generally perpendicularly and containing at least a plurality of vessel mounting structures, said vessel mounting structures having fittings for making fluidic connections to flexible tubing, and a plurality of flexible tubes for connecting said fittings of one vessel to another and to said rotary slide valve apertures and push-on connectors;
3) mounting at least one reactor vessel to said kit vessel mounting structure;
4) filling reagent vessels with predetermined reagents, adding fluidic seals, and mounting said vessels to said kit vessel mounting structure;
5) fluidically interconnecting said disposable kit rotary valves, push-on connectors, and vessel mounting structure fittings in a predetermined fluidic configuration;
6) making fluidic connections to said reagent vessels through said seals;
7) interfacing said disposable kit to said stationary processor; and
8) operating said processor to produce radiopharmaceuticals.

15. The method of claim 14 wherein steps 2–5 are preformed at a geographical location remote from said processor.

16. The method of claim 15 wherein steps 2–5 are performed at a central geographic location using a plurality of kits and distributed to a plurality of remote production facilities to carry out steps 6–8.

17. The method of claim 14 wherein said radiopharmaceutical is FDG.

18. The method of claim 14 where said disposable kits have a fluidic output fitting and a fluidic input fitting and the method further comprises, in step 7, interfacing one or more kits, each to a processor, and connecting outputs of one or more kits to inputs of other kits and, in step 8, operating two or more processors in sequence to produce a radiopharmaceutical.

19. The method of claim 14 further comprising the added steps of releasing said disposable kit into a shielded container and interfacing a second disposable kit to process a second batch of radiopharmaceuticals.

* * * * *